United States Patent [19]

Monnet et al.

[11] 3,930,498

[45] Jan. 6, 1976

[54] ANTI-ADHERENT MEDICAL DRESSINGS AND THE LIKE

[75] Inventors: Andre Monnet, Lyon; Maurice Cessiecq, Vernaison, both of France

[73] Assignee: Products Chimiques Ugine Kuhlmann, Paris, France

[22] Filed: Mar. 13, 1973

[21] Appl. No.: 340,667

[30] Foreign Application Priority Data
Mar. 14, 1972 France .............................. 72.08787

[52] U.S. Cl. ................................ 128/149; 128/156
[51] Int. Cl.² ................... A61B 19/00; A61L 15/00
[58] Field of Search ............ 128/156, 155, 157, 149

[56] References Cited
UNITED STATES PATENTS

| 2,477,403 | 7/1949 | Brady | 128/156 |
|---|---|---|---|
| 3,426,754 | 2/1969 | Bierenbaum | 128/156 |
| 3,686,725 | 8/1972 | Nisbet et al. | 128/156 |
| 3,709,221 | 1/1973 | Riely | 128/156 |

*Primary Examiner*—Lawrence W. Trapp
*Attorney, Agent, or Firm*—Pennie & Edmonds

[57] ABSTRACT

Anti-adherent material for coming into contact with the epidermis such as sheets, surgical dressings, various kinds of bandages and the like are disclosed which comprise a homopolymer or copolymer of tetrafluoroethylene containing at least about 50% tetrafluoroethylene deposited upon a support material which is resistant to the fritting temperature of the homopolymer or copolymer, the support material containing from about 25 to 90% homopolymer or copolymer and from 10 to 75% support material and possessing regularly disposed perforations for from about 0.1 to 10% of the surface thereof.

5 Claims, 4 Drawing Figures

ANTI-ADHERENT MEDICAL DRESSINGS AND THE LIKE

BACKGROUND OF THE INVENTION

I. Field of the Invention

This invention relates to the field of anti-adherent, i.e., non-sticking, materials for coming into contact with the epidermis such as medical dressings, hospital linens, surgical dressings, various types of bandages and so forth.

The anti-adherent materials made in accordance with this invention are especially useful for placement beneath the bodies of hospital patients due for prolonged bed-confinement. Patients suffering from serious injuries, in particular, widespread burns or wounds which heal only with considerable difficulty can benefit greatly from the application of the dressings of this invention.

II. Description of the Prior Art

It is known that cutaneous wounds covering a large body surface area are particularly difficult to heal and are highly subject to infection. The dressings or sheets coming into contact with such wounds often cause partial destruction of the epidermis resulting from removing the patient from the sheets or changing the patient's dressings. The risk of septicemia is particularly increased since the dressings are maintained about the would in a warm and wet condition due to the suppuration of the wound. Moreover, contact of long duration of sheets and patient's healthy epidermis can lead to the formation of scabs. It is also known that all of these phenomena are the source of pains which at times are very severe for the hospitalized.

In order to remedy the disadvantage resulting from the suppuration of wounds, exposure of the latter to air at ambient temperature is generally recognized as favorable but it is not always possible to do this with the materials now in existence due to their abrasive action against the epidermis during healing.

Various materials have been proposed to remedy these disadvantages and are presently being used in hospitals as materials for coming into contact with patients' body surfaces, as for example, non-woven sheets of absorbant fibers having a surface coating of a permeable resin such as polypropylene or a surface which has been aluminized by the deposition of a layer of aluminum powder.

These materials represent a significant improvement over the previously employed sheets and dressings made of natural or synthetic textiles, however, they possess the major disadvantage of not being sufficiently anti-adherent. As a result such materials still have a tendency to stick to injured epedermis, either during renewal of the skin by grafting or in the natural manner, and cause deterioration of the epidermis as a result of its being unavoidably torn away.

Moreover, these materials can be used only once since they are not washable or capable of being sterilized and thus their use is economically undesirable.

SUMMARY OF THE INVENTION

As a result of studies carried out in connection with hospitals specializing in the treatment of serious burns, the antiadherent materials of this invention were developed.

The anti-adherent medical dressings, sheets, bandages and the like of this invention comprise a homopolymer or copolymer of tetrafluoroethylene containing at least about 50% tetrafluoroethylene (hereinafter designated PTFE) deposited upon any suitable support material which is resistant to the fritting temperature of the PTFE, about 380°C, in such a way that the finished material will contain from about 25 to 90% of PTFE for about 10 to 75% of the support material by weight and from about 0.1 to 10% of the useful surface of the support material will be perforated thus permitting evacuation of the liquids tending to be secreted from patients' wounds.

The materials of this invention possess excellent antiadherent properties and show themselves to be very interesting for clinical use. Moreover, they are readily washable and capable of being sterilized and so can be used numerous times rendering them economical.

DESCRIPTION OF THE PREFERRED EMBODIMENTS

Figure 1:
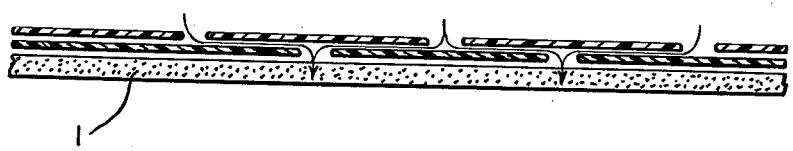
FIGS. 1 to 4 each illustrate a sectional view of an antiadherent medical dressing according to this invention.

According to one particularly interesting embodiment of this invention, a material comprising glass fiber having a surface area of 400 gm/m$^2$ is charged through impregnation with a dispersion of PTFE and then dried and heated in such a manner as to provide a product having a smooth and uniform surface containing from about 50 to 80% PTFE and from about 20 to 50% glass fiber and perforated with circular holes of about 1 to 6 mm diameter regularly disposed throughout the surface of the material so that the ratio of perforated surface area to material surface area is from about 1:1000 to 1:10.

This material can be used as such to provide articles supporting the sick or certain injured members, as for example, various hammocks or suspension devices, or they can be placed upon absorbtive layers such as sheets or blankets of the conventional type, or upon sheets made of non-woven cellulosic material. After use, the material can be washed and sterilized using any appropriate means. For example, sterilization can be carried out by heating or by passage through a sterilizing bath followed by drying. The article thus treated is ready for another use and is therefore stored in a sterile location.

It is especially advantageous to utilize a support material comprising two superimposed layers of a material such as recited above in such a way that the perforations are disposed in a regular manner so as to avoid contact of the epidermis with the absorptive layer placed beneath the support material. One interesting embodiment comprises using as the bottom layer an article having a somewhat rough or irregular surface. This will permit channeling of the liquids accumulating between the two superimposed layers. This can be accomplished by employing a bottom layer of glass fiber which is relatively coarse and contains less PTFE.

One embodiment of this invention, besides use in hospitals, is especially advantageous for use in transporting the injured by ambulance or for use in home-treating of the sick and injured. Articles conforming to this particular embodiment comprise one or two layers of an anti-adherent material according to the invention removably fastened employing any appropriate means to an absorptive substrate, for example, cellulosic fiber or non-woven cellulosic cloth. The assembly is placed in a sterile package following sterilization for convenient transport. Articles of this kind can therefore constitute part of the first-aid materials carried by ambulances and can also be used for home-treatment.

More specifically, the support materials according to this invention can be:

light materials of a weight in the range of about 50 gm/m² to 400 gm/m² for use in the preparation of sheets and various dressings applied to an absorptive layer which is places upon a support material such as padding or cushioning.

heavy materials of a weight in the range of about 400 gm/m² to 1000 gm/m² for use in the manufacture of articles employed only as hammocks and suspension devices.

The selection of a specific support material, homopolymer or copolymer and the amount to be applied to the support material and the extent of the perforations on the surface of the support material depend upon the nature of the end-use of the final product as is clearly evident to one skilled in the art.

The woven and non-woven materials which are resistant to the fritting temperature of PTFE, generally about 380°C, can be employed for the manufacture of the medical dressings herein. The use of glass fibers has been found to be of particular interest by virtue of their excellent comparability under actual conditions of use with PTFE and because of the wide range of commercially available products of this type. However, asbestos fibers or thermostable fibers such as fibers made from the aromatic polyamides, the imide polyamides and the imide polyesters are also useful.

All of the known and conventional dispersions of PTFE are useful for preparing these contacting materials but the most interesting results have been obtained with dispersions in which the particle size is less than about 1 micron. Dispersions of PTFE charged with such appropriate mineral charges as graphite and aluminum are especially advantageously used to improve certain characteristics of the contacting material, for example, they impart a certain degree of conductivity which will avoid the accumulation of static electricity. One can also impart to the materials any appropriate coloration by pigmenting the PTFE with pigments which are resistant to the fritting temperature of the polymer.

Instead of using a homopolymer of PTFE as the starting material, one can also use dispersions of TFE copolymers with copolymerizable monomers such as ethylene and hexafluoropropylene with a level of at least 50% of tetrafluoroethylene in the copolymer.

The following examples are illustrative of the medical dressings according to this invention.

EXAMPLE 1

A glass fiber cloth weighing 90 gm/m² and having a thickness of 0.06 mm was coated with an aqueous dispersion of PTFE supplied by the Societe des Produits Chimiques Ugine Kuhlmann under the trade name Soreflon 60 and containing 60% by weight of solid polymer in the form of fine spherical particles of 0.2 to 0.3 µ diameter and 3% nonionic dispersing agent.

This dispersion was diluted to provide 50% solids and the glass fiber was continuously coated by passage through an emulsion bath followed by drying at 100° to 120°C, vaporization of the wetting agent at 300°C and finally, fritting of the PTFE at 380° to 400°C. This operation was repeated four times to provide a thickness of 0.09 mm thus corresponding to a charge of 75% PTFE based on the total weight of coated fiber.

A coated material was then perforated with holes of 4 mm diameter disposed in staggered arrangement and spaced 45 mm in the transversal direction and 30 mm in the longitudinal direction.

The material was coated in the form of a rectangle having dimensions appropriate to the size of a conventional hospital bed. The four corners of this rectangle were provided with metal eyelets for attachment of the rectangle by means of straps. This article, sterilized and then placed upon a bed above a layer of absorptive cotton provide an excellent support for the injured having cutaneous injuries over a wide area. This support can also be employed as a sheet for surgical operations and results in the avoidance of scabs on the sick who will be subjected to long bed-confinement.

EXAMPLE 2

A material identical to that utilized in EXAMPLE 1 was coated with three layers of PTFE and was perforated according to the procedure indicated in EXAMPLE 1. A fourth layer was then applied in such a way that the deposition of polymer would moderate the sharp angles produced on the periphery of the perforations due to cutting.

This material was utilized as described in EXAMPLE 1 but provided superior comfort to especially sensitive epidermal tissue.

EXAMPLE 3

A sufficient surface of the material described in EXAMPLE 1 was cut in order to cover a surface of grafted skin. After sterilization the material was coated with PTFE and was applied directly to the epidermis and to cover the usual dressing. The interposition of the material coated with PTFE avoids the partial tearing away of the skin upon change of the dressing due to its anti-adherency.

EXAMPLE 4

Two layers of glass material coated with PTFE according to EXAMPLE 1 are superimposed, as shown in FIG. 1, in such a way that the holes do not correspond. The assembly constitutes a hospital sheet utilized upon an absorptive layer but permits drainage of liquids and the drying up of wounds without the skin being in contact with the absorptive material lying beneath the perforations in the material.

EXAMPLE 5

Figure 2:
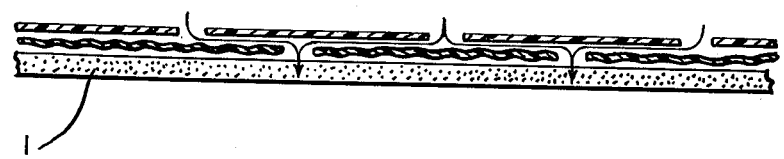

Following the procedure of EXAMPLE 4 but using as a lower support material a heavier glass cloth, weighing 320 gm/m² and 0.05 mm thickness, the cloth was coated with two layers of Soreflon 60 in such a way as not to destroy its surface irregularities. In this manner according to the diagram in FIG. 2, a material was obtained wherein the upper layer possessed a smooth surface and the lower layer possessed a rough surface thereby providing improved ability for drainage of the liquids which can thus pass more easily from an orifice to the other side despite their nonjuxtaposition.

EXAMPLE 6

Following the procedure set forth in EXAMPLE 1, glass fiber cloth weighing 400 gm/m² was coated with a dispersion of Soreflon 60 containing PTFE particles having a diameter between 0.1 and 0.3μ and containing 60% by weight of solid polymer in such a way as to provide a six-passage coating of PTFE equivalent to 68% by weight of the total amount of the finished material. This cloth which had a thickness of about 0.4 mm was perforated in its central portion with holes of 2 mm diameter spaced 10 mm in two directions so as to provide on its side a margin of 10 cm which was not perforated.

Figure 3:
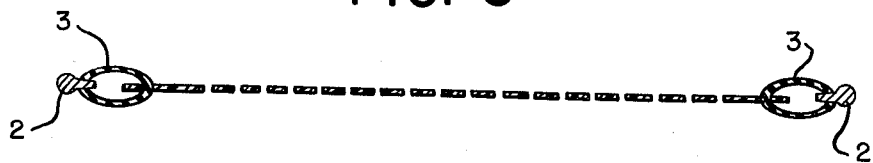

A length of the material sufficient for application by one who has been injured was cut from this material and its margin provided with eyelets of stainless steel spaced 10 cm apart. This material was then stretched in a metallic frame 2 while using elastic straps 3. The assembly constitutes a fixed or mobile support for the rest or transportation of the sick and injured as shown in FIG. 3.

EXAMPLE 7

Figure 4:

A supportive assembly was prepared as shown in FIG. 4 by superimposing two layers of glass cloth coated with PTFE prepared according to EXAMPLE 4 and a layer of absorptive cellulose.

The cellulose was maintained in permanent contact with the supportive layers by means of a glass fiber thread coated with PTFE 4. The asembly was joined together with a series of rivets 5 and studs 6 made of stainless steel in such a manner that the coated glass fiber cloth can be detached from the cellulosic part for the purposes of cleaning and reusing.

This assembly was sterilized and placed in a sterile container in such a way that it could be used in any place for the support of the injured or for their transportation by any appropriate means.

We claim:

1. Anti-adherent materials for coming into contact with the epidermis such as sheets, surgical dressings, various kinds of bandages and the like which comprise a homopolymer or copolymer of tetrafluoroethylene containing at least about 50% tetrafluoroethylene deposited upon a support material which is resistant to the fritting temperature of the homopolymer or copolymer, said anti-adherent materials containing from about 25 to 90% homopolymer or copolymer and from 10 to 75% support material and possessing regularly disposed perforations comprising about 0.1 to 10% of the surface.

2. Anti-adherent medical dressings according to claim 1 wherein the support material is made of glass fiber.

3. Anti-adherent medical dressings according to claim 1 made up of two layers of superimposed support material such that the perforations are interposed in a regular manner.

4. Anti-adherent medical dressings according to claim 1 disposed upon an absorptive substrate.

5. A method for contacting epidermis with anti-adherent materials such as sheets, surgical dressings, various kinds of bandages and the like which comprises contacting epidermis with a homopolymer or copolymer of tetrafluoroethylene containing at least about 50% tetrafluoroethylene deposited upon a support material which is resistant to the fritting temperature of the homopolymer or copolymer, said anti-adherent material containing from about 25 to 90% homopolymer or copolymer and from 10 to 75% support material and possessing regularly disposed perforations comprising about 0.1 to 10% of the surface.

* * * * *

UNITED STATES PATENT AND TRADEMARK OFFICE
CERTIFICATE OF CORRECTION

PATENT NO. : 3,930,498
DATED : January 6, 1976
INVENTOR(S) : ANDRE MONNET ET AL.

It is certified that error appears in the above-identified patent and that said Letters Patent are hereby corrected as shown below:

First page, the "Assignee" should read -- Produits Chimiques Ugine Kuhlmann, Paris, France --.

Column 1, line 65, "antiadherent" should read -- anti-adherent --.

Column 2, lines 12 and 13, "antiadherent" should read -- anti-adherent --.

Column 3, line 11, "places" should read -- placed --.

Column 4, line 14, "provide" should read --, provides --.

Signed and Sealed this first Day of June 1976

[SEAL]

Attest:

RUTH C. MASON
*Attesting Officer*

C. MARSHALL DANN
*Commissioner of Patents and Trademarks*